(12) United States Patent
Sprecker et al.

(10) Patent No.: US 6,495,497 B1
(45) Date of Patent: Dec. 17, 2002

(54) USE OF 4-ETHYLOCTANAL IN PERFUME COMPOSITIONS

(75) Inventors: Mark A. Sprecker, Sea Bright, NJ (US); Richard Anthony Weiss, Livingston, NJ (US); Manfred Pawlak, Princeton, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 09/964,830

(22) Filed: Sep. 26, 2001

(51) Int. Cl.[7] .............................. C11D 3/50; A61K 7/46
(52) U.S. Cl. ........................................ 510/101; 512/27
(58) Field of Search .............................. 510/101; 512/27

(56) References Cited

U.S. PATENT DOCUMENTS 4,534,891 A    8/1985  Boden et al.
4,922,028 A  *  5/1990  Oswald et al. .............. 568/448

FOREIGN PATENT DOCUMENTS

WO    WO 00/33956    *  6/2000

OTHER PUBLICATIONS

Weitzel, G., et al; HSZPZAZ; Hoppe–Seyler's Z. Physiol.Chem.; GE; 353; 1972, pp. 641–653.

Weitzel, et al, "Additional Tumor–Inhibiting Compound Classes, V[1–4] Cytostatic Properties of Alkyl–Branched Alcohols and Aldehydes with a Chain Length of C8", Institute of Physiological Chemistry of Tubingen University, Z. Physiol.Chem., 353:641–653, Apr. 1972.

* cited by examiner

Primary Examiner—John Hardee
(74) Attorney, Agent, or Firm—Joseph F. Leightner

(57) ABSTRACT

The use of 4-ethyloctanal as a fragrance chemical, suitable for use in creating fragrance, and scents in items such as perfumes, colognes and personal care products is disclosed.

7 Claims, No Drawings

USE OF 4-ETHYLOCTANAL IN PERFUME COMPOSITIONS

FIELD OF THE INVENTION

The use of 4-ethyloctanal is disclosed as a fragrance chemical suitable for incorporation in fine fragrances, cosmetics, toiletries and related applications.

BACKGROUND OF THE INVENTION

There is an ongoing need in the fragrance industry to provide new chemicals to give perfumers and other persons ability to create new fragrances for perfumes, colognes and personal care products.

The preparation of the compound 4-ethyloctanal is disclosed by Weitzel, G. et al; HSZPZAZ; Hoppe-Seyler's Z. Physiol.Chem.; GE; 353; 1972, pages 641–653. The authors disclose the preparation of the compound by the dehydrogenation of the corresponding alcohol to the aldehyde. This article is silent as to odor of the compound or the suitability of the compound to be employed as a fragrance chemical.

SUMMARY OF THE INVENTION

The present invention is directed to the use of 4-ethyloctanal as a fragrance chemical to enhance fragrance in perfumes, toilet waters, colognes, personal products and the like. More specifically, the present invention is a method for enhancing a perfume by incorporating an olfactory acceptable amount of compounds of the formula:

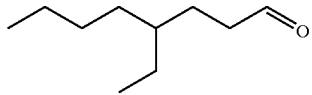

These and other embodiments of the present invention will be apparent by reading the following specification.

DETAILED DESCRIPTION OF THE INVENTION

The present invention is directed to the use of the compound, 4-ethyloctanal in fragrance formulations. The preparation of the compound, 4-ethyloctanal is described in Weitzel, G. et al; HSZPZAZ; Hoppe-Seyler's Z. Physiol.Chem.; GE; 353; 1972, pages 641–653.

We have discovered that 4-ethyloctanal has an orange, costus odor or note, that is well suited for use as a fragrance chemical.

The use of this compound is widely applicable in current perfumery products, including the preparation of perfumes and colognes, the perfuming of personal care products such as soaps, shower gels, and hair care products as well as air fresheners, candles and cosmetic products. The compound can also be used to perfume candles and cleaning agents, such as, but not limited to soaps, detergents, dishwashing materials, scrubbing compositions, window cleaners, and the like.

In these preparations, the compound of the present invention can be used alone or in combination with other fragrance compositions, solvents, adjuvants and the like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, and carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.1 to about 8 and most preferably from about 0.5 to about 5 weight percent. In addition to the compounds, other agents can be used in conjunction with the fragrance. Well known materials such as surfactants, emulsifiers, and polymers to encapsulate the fragrance can also be employed without departing from the scope of the present invention.

Another method of reporting the level of the compound of the invention in the perfumed composition, i.e., the compounds as a weight percentage of the materials added to impart the desired fragrance. The compounds of the invention can range widely from 0.005 to about 10 weight percent of the perfumed composition, and preferably from about 0.1 to about 5 weight percent. Those with skill in the art will be able to employ the desired level of the compound of the invention to provide the desired fragrance and intensity.

The following are provided as specific embodiments of the present invention. Other modifications of this invention will be readily apparent to those skilled in the art, without departing from the scope of this invention. As used herein all percentages are weight percent. IFF as used in the examples is understood to mean International Flavors & Fragrances Inc., DPG is understood to mean dipropylene glycol, DEP is understood to mean diethylphthalate.

EXAMPLE 1

Incorporation of a 4-ethyloctanal in a fragrance formulation:

| Material | Parts |
|---|---|
| TRIPAL (IFF) | 4.5 |
| AMBRETTOLIDE 1% in DPG (IFF) | 30 |
| ARTEMISIA oil (Robertet) | 5 |
| BOISAMBRENE FORTE 10% in DPG (Henkel) | 90 |
| Citronellol Coeur | 40 |
| Alpha-damascone 10% DEP (Firmenich) | 1 |
| Dimethyl benzyl carbinyl butyrate | 2 |
| DPG | 88 |
| 4-Ethyloctanal | 20 |
| FLOROL (Firmenich) | 6 |
| FRUCTONE (IFF) | 11 |
| DYNASCONE 1% (DPG) | 60 |
| Ginger Chinese extract | 1 |
| Iso Cyclo Citral 10% in DPG (IFF) | 1 |
| KOAVONE (IFF) | 36 |
| LIFFAROME "PFG" 10% in DPG (IFF) | 40 |
| Litsea cubeba oil | 15 |
| MAGNOLAN (H & R) | 9 |
| Magnolia flower oil 10% in DEP | 4 |
| OXANE 1% in DPG (Firmenich) | 5 |
| Phenyl acetaldehyde | 2.5 |
| Phenyl ethyl alcohol | 130 |
| Rose oxide 10% in DPG | 13 |
| TRIFERNAL (Firmenich) | 1 |
| VELOUTONE 10% in DPG (Firmenich) | 25 |

The above formulation was described as having a green, floral note, partially through the incorporation of the 4-ethyloctanal.

The above fragrance formulations are presented to demonstrate the effectiveness of the compounds of the present invention in enhancing, improving or modifying the performance of the formulations in which they are incorporated.

What is claimed is:

1. A method for improving, enhancing or modifying a fragrance through the addition of an olfactory acceptable amount of 4-ethyloctanal.

2. The method of claim 1 wherein the fragrance is incorporated into a product selected from perfumes, colognes, candles, toilet waters, cosmetic products, personal care products, fabric care products, cleaning products and air fresheners.

3. The method of claim 2 wherein the cleaning product is selected from the group consisting of soaps, detergents, dishwashing compositions, scrubbing compounds and window cleaners.

4. The method of claim 2 wherein the product is a personal care product.

5. The method of claim 1 wherein the level is from about 0.005 to about 10 weight percent.

6. The method of claim 1 wherein the level is from about 0.1 to about 8 weight percent.

7. The method of claim 1 wherein the level is from about 0.5 to about 5 weight percent.

* * * * *